United States Patent [19]

McClain

[11] Patent Number: 5,302,681
[45] Date of Patent: Apr. 12, 1994

[54] POLYMERIZATION INHIBITION BY FULLERENES

[75] Inventor: Robert D. McClain, Houston, Tex.

[73] Assignee: Nalco Chemical Company, Naperville, Ill.

[21] Appl. No.: 989,933

[22] Filed: Dec. 10, 1992

[51] Int. Cl.$^5$ .................. C08F 36/08; C08F 12/08; C07C 7/20

[52] U.S. Cl. .................. 526/340.2; 526/346; 526/335; 526/328; 526/297; 526/341; 526/342; 526/319; 526/170; 526/173; 526/210; 526/217; 526/225; 558/304; 558/306; 558/307; 560/4; 585/2

[58] Field of Search .................. 526/89, 340.2, 346

[56] References Cited

PUBLICATIONS

Article Entitled "Electron Spin Resonance Study of the Radical Reactivity of $C_{60}$" by Krusic, et al; American Chemical Society, vol. 113, No. 16, 1991 pp. 6274-6275.
Article Entitled "$C_{60}$: Buckminsterfullerene" by Kroto, et al; Chemical Reviews vol. 91, No. 6, 1991, pp. 1213-1235.
Article Entitled "$C_{60}$ as a Radical Sponge" by McEwen, et al, American Chemical Society, vol. 114, No. 11, 1992, pp. 4412-4415.
Article Entitled "Synthesis of a $C_{60}$-p-Xylylene Copolymer" by Loy, et al, American Chemical Society, vol. 114, 1992, pp. 3977-3978.
Article Entitled "Systematic Chemistry of $C_{60}$ Beginning To Emerge" by Rudy Baum, C&EN, 1991, pp. 17-20.
Article Entitled "Great Balls of Carbon" by Brian Nadel, Chemical Business, 1992, pp. 15-17.
Article Entitled "Buckyballs: Wide Open Playing Field For Chemists", Science, vol. 254, 1991, pp. 1706-1707.
Article Entitled "The Chemical Properties of Buckminsterfullerene ($C_{60}$) and the Birth and Infancy of Fulleroids" by Fred Wudl; Acc. Chem. Res. 1992, vol. 25, pp. 157-161.
Article Entitled "Radical Reactions of $C_{60}$" by Krusic, et al; Science, 1991; vol. 254, pp. 1183-1185.
Article Entitled "Fullerenes" by Curl, et al; Scientific American, 1991, pp. 54-63.

Primary Examiner—Joseph L. Schofer
Assistant Examiner—Mark Nagumo
Attorney, Agent, or Firm—Bush, Moseley & Riddle

[57] ABSTRACT

The premature free-radical polymerization of a non-linear, readily polymerizable organic monomer under conditions where the monomer would otherwise polymerize is inhibited by incorporating within the non-linear, readily polymerizable monomer a polymerization inhibiting amount of a fullerene or a derivative thereof.

21 Claims, No Drawings

POLYMERIZATION INHIBITION BY FULLERENES

FIELD OF THE INVENTION

This invention relates to a method of inhibiting the premature, free-radical polymerization of non-linear, readily polymerizable monomer by intimately mixing with the monomer of polymerization inhibiting amount of a fullerene compound.

BACKGROUND OF THE INVENTION

A significant portion of the petrochemical industry is based on the production and utilization of polymerizable monomeric compounds. A wide variety of monomers are useful as precursors of polymeric products including a number of organic monomers which are particularly easy to polymerize. Certain of these readily polymerizable monomers are particularly reactive because of the presence within the monomeric molecule of an activated ethylenic bond, i.e., a non-aromatic carbon-carbon double bond which is activated by conjugation with other multiple bonds between adjacent atoms. Illustrative of polymers produced from such polymerizable monomers are the polystyrenes of the plastics industry and the polyalkadienes and polynitriles of the elastomer industry. The presence of the activated ethylenic unsaturation in the readily polymerizable monomers enables polymerization of the monomers to be conducted under rather mild but carefully controlled conditions and the polymeric products have well established utility.

However, the readily polymerizable monomers often undergo undesirable polymerization, e.g., polymerization prior to the time polymerization is intended, as during the production, purification, storage or handling of the monomers, when exposed to free radicals resulting from the presence of oxygen and other free radical sources. This premature free-radical polymerization can have significant consequences since the polymer formed tends to foul or even plug the mechanical equipment used in the production, purification, handling or even storage of the monomer unless precautions are taken to inhibit or prevent the polymerization. The premature polymerization typically produces polymer product of inferior quality and can be a safety hazard if operating equipment becomes plugged.

To prevent or at least retard the premature free-radical polymerization of readily polymerizable monomers it is conventional to add to the monomer a small but effective amount of an antioxidant or inhibitor. Many if not most of the conventional polymerization inhibitors are complex organic compounds containing functional groups with atoms of oxygen, nitrogen or sulfur. The presence of these atoms in conventional polymerization inhibitors does lead to some disadvantages. The presence of the oxygen, nitrogen or sulfur atoms frequently renders the inhibitor toxic to animal life and can result in the poisoning of polymerization catalysts or molecular sieves used in the subsequent processing and polymerization of the readily polymerizable monomer. It would be of advantage, therefore, to have polymerization inhibitors which have little or no content of the oxygen, nitrogen or sulfur atoms which lead to toxicity or processing problems.

SUMMARY OF THE INVENTION

The present invention provides an improved method for the inhibition of the premature free-radical polymerization of non-linear, readily polymerizable organic molecules. More particularly, the invention provides a method for inhibiting such polymerization under conditions where the premature polymerization would likely take place by incorporating within the non-linear, readily polymerizable monomer a polymerization inhibiting amount of a fullerene compound. The invention also provides compositions inhibited against free-radical polymerization, which compositions comprise at least one non-linear, readily polymerizable organic monomer and an inhibiting quantity of a fullerene compound.

DESCRIPTION OF THE INVENTION

The fullerene compound employed as free-radical polymerization inhibitor in the present invention is a fullerene or a substituted fullerene, i.e., a fullerene derivative. Mixtures of fullerenes and/or substituted fullerenes are also satisfactory. The class of unsubstituted fullerenes comprises a recently-discovered third class of pure carbon in addition to diamond and graphite. A fullerene is characterized as having only atoms of carbon and an even number of carbon atoms of as few as 24 atoms and as high as 600 atoms or even higher. The fullerenes are further characterized by a generally spherical, hollow shape composed of carbon atoms arranged in hexagons with some pentagons also present. The most widely studied member of the class is the fullerene of 60 carbon atoms arranged as a hollow ball. The family name of "fullerene" originates from the similarity of models of the fullerene of 60 carbon atoms, termed fullerene-60 or $C_{60}$, to the geodesic dome originated by Buckminister Fuller. The particular compound $C_{60}$ is further known as buckministerefullerene as the class of compounds has trivially been termed "Buckyballs". Also studied extensively is $C_{70}$, the fullerene containing 70 carbon atoms in a hollow molecule somewhat distorted from the spherical. A rather extensive review article on fullerenes and fullerene compounds is provided by Kroto et al, Chem. Rev., 91, pp 1212–1235 (1991) incorporated herein by reference. This publication illustrates the configuration of a number of fullerenes ranging from $C_{28}$ to $C_{540}$. The fullerenes are produced by methods now well known as described by Kroto et al.

The fullerene, although pure carbon, are reactive and fullerene derivatives useful in the invention include derivatives which contain metal, alkyl including aralkyl, aryl, hydroxyl, halo, alkoxy, amino, nitro and carbophenoxy moieties within the fullerene derivative molecule. Metal derivatives of fullerenes include those molecules with metal encapsulated or "trapped" within the spherical, hollow fullerene molecule. By way of illustration, compounds of the structure $C_{60}M$ are known wherein M is alkali metal or transition metal. Illustrative are $C_{60}K$, $C_{60}Rb$, $C_{60}Cs$, $C_{60}La$, $C_{60}Y$ and $C_{60}U$, as disclosed by Baum, Chemical & Engineering News, pp 17–20, Dec. 16, 1991. The fullerenes also react to produce ionic compounds such as $K_3 C_{60}$ disclosed by Curi et al, Scientific American, pp 54–63, October, 1991. Other compounds of this type are shown by the above Kroto et al article and the references cited therein.

The fullerenes are reactive towards a number of organic free radicals to introduce organic substituents onto the fullerene molecule. One such free radical is the benzyl free radical and benzylation of $C_{60}$ introduces as many as 15 benzyl radicals onto the fullerene. See, for example, Krusic et al, Science, 254, pp 1183-1185 (1991). Alkylation to introduce alkyl groups onto the fullerene structure is reported by McEwen et al, J. Am. Chem. Soc., 114, pp 4412-4414 (1992).

A variety of other free radical compounds introduces a variety of other substituents. The above Baum article, and references cited therein, discloses $C_{60}$ molecules with up to 15 hydroxyl substituents. The Baum reference also shows reaction of $C_{60}$ with ethyl diazoacetate to produce a fullerene derivative with 61 carbon atoms and a carboethoxy substituent. Reaction of other diazo compounds [see Wudl, Acc. Chem. Res., 25, pp 157-161 (1992)] produces similar $C_{61}$ derivatives, termed "fulleroids", with halo, alkoxy, amino, nitro and carbophenoxy substituents. From these substituted fullerenes are produced other fullerene compounds with other substituents, e.g., sulfonate, carboxy, ammonium, thiol and phosphine, by conventional methods.

Of particular interest as polymerization inhibitors of the invention are the fullerenes of from about 32 to about 300 carbon atoms and the derivatives thereof with alkyl, aryl, hydroxyl, amino or ammonium, sulfonate, metal and halo substituents. These substituent groups tend to modify the physical properties of the fullerene compounds and therefore the solubility characteristics of the fullerene compounds in the media of application. For example, a fullerene derivative having benzyl, phenyl or alkyl substituents would be more soluble in aromatic solvents and substitution of a fullerene by metal, ammonium or sulfonate groups will increase the solubility of the fullerene compound in aqueous media. Particularly preferred as the polymerization inhibitor are fullerenes of 32 to 300 carbon atoms inclusive, especially $C_{60}$ and $C_{70}$.

The non-linear, readily polymerizable organic compounds whose free-radical polymerization is inhibited by the fullerene compounds of the invention are characterized by an ethylenic linkage, i.e., a carbon-carbon double bond, which is activated by conjugation with multiple bonds between adjacent atoms, and at least one carbon atom which is attached to at least three other carbon atoms. Thus, at least one carbon atom of the non-linear, readily polymerizable monomer is involved in carbon skeleton branching or ring formation. Illustrative of such non-linear, readily polymerizable monomers are A. Alkenylaromatic compounds of up to 20 carbon atoms inclusive such as styrene, α-methylstyrene, p-methylstyrene and vinylnaphthalene;

B. Conjugated alkadienes of up to 8 carbon atoms inclusive such as isoprene and 2-methyl-1,3-pentadiene;

C. $\alpha,\beta$-Unsaturated nitriles of up to 8 carbon atoms inclusive such as methacrylonitrile and ethacrylonitrile; and D. $\alpha,\beta$-Unsaturated carboxylic acid esters of up to 20 carbon atoms inclusive such as methyl methacrylate and ethyl methacrylate.

The process of the invention is also suitably employed to inhibit the free-radical polymerization of mixtures on non-linear, readily polymerizable monomers. Best results are obtained when the fullerene compounds of the invention are employed to inhibit the free-radical polymerization of vinylaromatic compounds, especially styrene, or of branched alkadienes, especially isoprene. A particularly preferred application of the method of the invention is in the inhibition of undesirable styrene polymerization.

The fullerene compound is employed to retard the premature free-radical polymerization of non-linear, readily polymerizable monomer by mixing the fullerene compound and monomer at or prior to subjecting the monomer to conditions, including conditions of elevated temperature and pressure, where the monomer is likely to encounter extraneous free radicals and undesirably polymerize. In one modification, the fullerene compound is added to the non-linear, readily polymerizable monomer as the monomer is separated from materials encountered during the production of the monomer. By way of illustration, isoprene is conventionally produced by operation of an ethylene cracker and is separated from other products at elevated temperature. Provision of a fullerene compound serves to retard undesirable polymerization during and after the separation. In an alternate modification, a fullerene compound is provided to unreacted monomer as the monomer is separated from a polymerization product and recycled to the polymerization reactor. In yet another modification, the fullerene compound is added to non-linear, readily polymerizable monomer during shipping or storage of the monomer prior to utilization in a polymerization process or other use.

Independent of the particular application, the fullerene compound is utilized to retard free-radical polymerization by intimately mixing the fullerene material with the non-linear, readily polymerizable monomer in an amount effective to retard premature or undesirable polymerization. The methods of producing the intimate mixture are conventional and include shaking and stirring. The effective amount of fullerene compound to retard undesirable free-radical polymerization is from about 15 ppm to about 2000 ppm of fullerene based on the total mixture of fullerene compound and non-linear, readily polymerizable monomer. Better results are obtained when the amount of fullerene compound to be provided to the readily polymerizable monomer is from about 500 ppm to about 1000 ppm on the same basis.

The presence of the fullerene compound in the mixture with at least one non-linear, readily polymerizable monomer prevents or at least retards the premature free-radical polymerization of the polymerizable monomer. Even the formation of small amounts of polymer during the storage or processing of the non-linear, readily polymerizable monomer in the presence of the fullerene compound will not unduly adversely effect such storage or processing since polymer formed in the presence of the fullerene compound tends to be of relatively low molecular weight. These low molecular weight polymer are likely soluble in the excess of readily polymerizable monomer and do not plug or excessively foul the mechanical equipment employed in the storage or handling of the readily polymerizable monomer. However, the presence of the fullerene compound is not unduly adverse when the intended polymerization of the non-linear, readily polymerizable monomer is desired. The fullerene compound is removed by conventional means such as extraction or absorption or the effect of the fullerene compound is overcome by the polymerization conditions including the provision of excess polymerization catalyst or by the use of a higher polymerization temperature.

The invention is further illustrated by the following illustrative Embodiment which also contains comparative data not of the invention. The illustrative Embodiment should not be regarded as limiting the invention.

ILLUSTRATIVE EMBODIMENT

A solution of fullerene was prepared from a mixed fullerene obtained from Aldrich Chemical Company, Catalog Number 37,712-D. The fullerene was 90% by weight $C_{60}$ and 10% by weight $C_{70}$. A quantity of this mixture, 250 mg, was dissolved in 53 g of toluene to produce a 0.0472% by weight solution.

To produce a non-inhibited styrene sample, 125 ml of commercial styrene inhibited with 50 ppm t-butylcatechol was added to a 500 ml separatory funnel. One molar potassium hydroxide, 125 ml, was added and the funnel was stoppered. The funnel and contents were taken vigorously and the contents were allowed to separate. The aqueous phase was drained from the funnel and 125 of 1M hydrochloric acid was added. The funnel was again stoppered and the funnel and contents were again shaken. The aqueous phase was again removed and the organic phase (styrene) was shaken with deionized water. The styrene was removed from the funnel and dried over sodium sulfate.

Ten milliter samples of this styrene were pipetted into each of 10 vials. To five of the vials, 1 ml of toluene was added and to the other five vials 1 ml of the fullerene/toluene solution produced above was added. The vials were then stoppered with foil-lined caps and placed in a large glass dish. The dish and vials were placed in an oven and maintained at 225° F. for 3 hours. The dish and vials were then removed and allowed to cool to room temperature in a fume hood. Each vial was then uncapped and approximately 10 ml of methanol were added to each. The contents of each vial were mixed vigorously with a spatula as a precipitate of polystyrene was formed. Each sample was repeatedly rinsed with methanol until the polystyrene precipitate was well-formed.

Each polystyrene sample was then dried in air on a watch glass to evaporate most of the residual methanol. The precipitates were then weighed in tared vials. After weighing, each vial was left uncovered in a fume hood for 2 days and the polystyrene samples were weighed again. The results of these weighings are found in the Table.

TABLE

| Vial No. | Additive | First Weight | Second Weight |
|---|---|---|---|
| 1 | toluene | 5.1010 | 4.5910 |
| 2 | toluene | 6.4392 | 5.8235 |
| 3 | toluene | 6.2447 | 5.6277 |
| 4 | toluene | 6.0485 | 5.5544 |
| 5 | toluene | 4.5857 | 3.9150 |
| 6 | fullerene/toluene | 1.7746 | 1.3928 |
| 7 | fullerene/toluene | 1.2185 | 0.9383 |
| 8 | fullerene/toluene | 1.0557 | 0.8129 |
| 9 | fullerene/toluene | 1.0327 | 0.8150 |
| 10 | fullerene/toluene | 0.8160 | 0.6392 |

From the above data, the average weight of the polystyrene formed in the samples where toluene was added (for comparison) was 5.10239. The average weight of the polystyrene formed when the styrene was inhibited with fullerene was 0.9196 g. Thus, approximately 82% of the styrene polymerization was inhibited by the presence of 472 ppm of mixed fullerene.

What is claimed is:

1. A process of inhibiting the premature free-radical polymerization of a non-linear, readily polymerizable organic monomer under conditions where the monomer would otherwise polymerize, which process comprises intimately mixing with the monomer a polymerization inhibiting, soluble amount of a fullerene compound.

2. The process of claim 1 wherein the monomer is alkenylaromatic compound, conjugated alkadiene, $\alpha,\beta$-unsaturated nitrile or $\alpha,\beta$-unsaturated carboxylic acid ester.

3. The process of claim 2 wherein the fullerene compound has from about 32 to about 300 carbon atoms inclusive and is a fullerene or a fullerene substituted with alkyl, aryl, hydroxy, amino or ammonium, sulfonate, metal or halo.

4. The process of claim 3 wherein the monomer is vinylaromatic compound or alkadiene.

5. The process of claim 4 wherein the fullerene compound is a fullerene.

6. The process of claim 5 wherein the monomer is isoprene.

7. The process of claim 5 wherein the monomer is styrene.

8. The process of claim 7 wherein the fullerene is $C_{60}$.

9. The process of claim 7 wherein the fullerene is $C_{70}$.

10. In the process of inhibiting the undesirable free-radical polymerization of a non-linear, readily polymerizable monomer under conditions where the monomer is likely to polymerize, which process comprises providing to the monomer a polymerization inhibiting, soluble quantity of a polymerization inhibitor, the improvement of using as polymerization inhibitor a fullerene compound.

11. The process of claim 10 wherein the fullerene compound is a fullerene or a fullerene substituted with alkyl, aryl, hydroxy, amino or ammonium sulfate, metal or halo.

12. The process of claim 11 wherein the fullerene compound is a fullerene.

13. The process of claim 12 wherein the fullerene has from 32 to 300 carbon atoms.

14. The process of claim 12 wherein the fullerene has 60 or 70 carbon atoms.

15. A composition inhibited against premature free-radical polymerization of a non-linear, readily polymerizable monomer which comprises an intimate mixture of the monomer and a polymerization inhibiting, soluble amount of a fullerene compound.

16. The composition of claim 15 wherein the monomer is alkenylaromatic compound, conjugated alkadiene, $\alpha,\beta$-unsaturated carboxylic acid ester, or $\alpha,\beta$-unsaturated nitrile.

17. The composition of claim 16 wherein the fullerene compound is a fullerene or a fullerene substituted with alkyl, aryl, hydroxy, amino or ammonium, sulfonate, metal or halo.

18. The composition of claim 16 wherein the fullerene compound is a fullerene of from 32 to 300 carbon atoms.

19. The composition of claim 18 wherein the monomer is styrene.

20. The composition of claim 18 wherein the monomer is isoprene.

21. In the process of producing a reduced quantity of polymer of non-linear, readily polymerizable monomer than would normally be produced under the free radical conditions where the monomers would polymerize, by providing to the monomer a polymerization inhibiting, soluble quantity of a polymerization inhibitor, the improvement of using as the polymerization inhibitor a fullerene compound, thereby obtaining a polymer of relatively low molecular weight.

* * * * *